US010954540B2

(12) United States Patent
Schwarz et al.

(10) Patent No.: US 10,954,540 B2
(45) Date of Patent: Mar. 23, 2021

(54) METHODS OF PRODUCING BIOSYNTHETIC BACTERIAL CELLULOSE MEMBRANES

(71) Applicant: The University of Iowa Research Foundation, Iowa City, IA (US)

(72) Inventors: Chaid Schwarz, Maple Grove, MN (US); Vijay Kumar, Iowa City, IA (US); Madhavan Raghavan, Coralville, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 137 days.

(21) Appl. No.: 16/061,151

(22) PCT Filed: Dec. 12, 2016

(86) PCT No.: PCT/US2016/066173
§ 371 (c)(1),
(2) Date: Jun. 11, 2018

(87) PCT Pub. No.: WO2017/100771
PCT Pub. Date: Jun. 15, 2017

(65) Prior Publication Data
US 2018/0355393 A1 Dec. 13, 2018

Related U.S. Application Data

(60) Provisional application No. 62/266,405, filed on Dec. 11, 2015.

(51) Int. Cl.
C12P 19/04 (2006.01)
A61L 15/28 (2006.01)
(Continued)

(52) U.S. Cl.
CPC .............. C12P 19/04 (2013.01); A61L 15/28 (2013.01); A61L 27/20 (2013.01); A61L 31/042 (2013.01);
(Continued)

(58) Field of Classification Search
CPC ........ A61Q 11/00; A61Q 19/00; A61Q 17/02; A61Q 17/04; A61P 1/02; A61P 17/00; A61P 17/02; A61P 17/16; A61P 31/02; A61P 31/04; A61P 31/10; A61P 35/00; A61P 15/00; A61P 15/02; A61P 29/00; A61P 9/00; A61K 8/20; A61K 8/23; A61K 8/731; A61K 8/8147; A61K 8/22; A61K 35/74; A61K 8/99; A61K 2300/00; A61K 9/2054; A61K 47/38; A61K 9/1652; A61K 8/371; A61K 9/0014; A61K 31/137; A61K 31/18; A61K 31/4545; A61K 31/58; A61K 9/2018; A61K 9/2027; A61K 9/4866; A61K 31/135; A61K 31/167; A61K 31/517; A61K 35/12; A61K 8/027; A61K 8/04; A61K 9/0024; A61K 9/1611; A61K 9/1623; A61K 9/1641; A61K 9/2009; A61K 9/2095; A61K 9/4816; A61K 9/485; A61K 9/4858; A61K 9/5042; A61K 31/192; A61K 31/473; A61K 31/506; A61K 36/48; A61K 47/12; A61K 9/0034; A61K 9/146; A61K 9/1635; A61K 9/2059; A61K 9/209; A61K 9/2846; A61K 9/2866; A61K 9/4808; A61K 9/5026; A61K 9/5073; A61K 9/7105; C01B 11/024; C08L 1/00; C08L 1/26; C08L 1/04; C08L 1/02; C08L 29/04; C08L 2666/26; C08L 97/02; A61L 15/28; A61L 27/20; A61L 31/042; A61L 27/507; A61L 27/38; A61L 27/56; A61L 15/225; A61L 27/48; A61L 31/10; A61L 31/129; A61L 2420/06; A23K 10/16; A23K 10/18; A23K 50/42; A23L 33/135; A61F 2/07; A61F 2/2415; A61F 2/2472; A61F 2200/0025; A61F 2240/001; A61F 2/86; A61F 2/95; C12N 11/00; C12N 2533/78; C12N 5/0068; C12N 19/04; C12N 15/8246; C12N 1/38; C12N 9/1059; C12P 19/04; C08B 15/00; C08B 30/12; C08B 37/00; C08B 15/02; C08B 3/00; C08B 15/04; C08B 15/10; A01N 25/10; G03F 7/039; G03F 7/2059; H01L 21/0277; Y10S 430/143; Y10S 435/823; Y10S 428/913; Y10S 435/822; A61B 2562/0215; A61B 5/0408; A61B 5/04085; A61B 5/6804;
(Continued)

(56) References Cited

U.S. PATENT DOCUMENTS 2,134,825 A * 11/1938 Hill ..................... C08B 15/06
536/30
4,942,128 A 7/1990 Brown, Jr.
(Continued)

FOREIGN PATENT DOCUMENTS

WO 2015040106 3/2015

OTHER PUBLICATIONS

Jatmiko et al, "Thin Layer Drying Model of Bacterial Cellulose Film",I 2017 IOP Conf. Ser.: Earth Environ. Sci. 101 012011 . (Year: 2017).*
(Continued)

Primary Examiner — Deborah K Ware
(74) Attorney, Agent, or Firm — Haugen Law Firm PLLP

(57) ABSTRACT

Described herein are methods of producing biosynthetic bacterial cellulose membranes having improved characteristics that are advantageous for use in various biological applications, including medicine.

17 Claims, 9 Drawing Sheets

(51) Int. Cl.
*A61L 27/20* (2006.01)
*A61L 31/04* (2006.01)
*C12N 11/00* (2006.01)
*A61F 2/07* (2013.01)
*A61L 27/50* (2006.01)

(52) U.S. Cl.
CPC ............... *C12N 11/00* (2013.01); *A61F 2/07* (2013.01); *A61L 27/507* (2013.01)

(58) Field of Classification Search
CPC ... B29C 39/025; B29C 39/10; B29K 2001/00; B29L 2031/7534; C07D 401/04; C21D 1/18; C22F 1/10; Y10T 29/49826; Y10T 428/2922; Y10T 428/2965; C12R 1/02; A01G 13/0262; A01G 2013/004; D06M 15/05
See application file for complete search history.

(56) References Cited

U.S. PATENT DOCUMENTS

| | | | |
|---|---|---|---|
| 5,846,213 A * | 12/1998 | Wan | A61F 13/00012 602/49 |
| 2002/0107223 A1 | 8/2002 | Oster et al. | |
| 2005/0106717 A1 | 5/2005 | Wilson et al. | |
| 2007/0053960 A1 | 3/2007 | Brown, Jr. | |
| 2008/0275231 A1 | 11/2008 | Zhang et al. | |
| 2010/0042197 A1 | 2/2010 | Bodin et al. | |
| 2011/0086236 A1 | 4/2011 | Catchmark et al. | |
| 2011/0319607 A1 | 12/2011 | Bertholdt et al. | |
| 2013/0224278 A1 | 8/2013 | Czaja et al. | |
| 2015/0044446 A1 | 2/2015 | Trexler et al. | |
| 2015/0051687 A1 * | 2/2015 | Dickerhoff | A61F 2/95 623/1.11 |

OTHER PUBLICATIONS

Anton-Sales et al, "Opportunities of Bacterial Cellulose to Treat Epithelial Tissues" Current Drug Targets, 2019, 20, 808-822. (Year: 2019).*
Search Report and Written Opinion for international application serial No. PCT/US2016/066173 dated Feb. 24, 2017.
Qi, H., Cai, J., Zhang, L. & Kuga, S. Properties of films composed of cellulose nanowhiskers and a cellulose matrix regenerated from alkali/urea solution. Biomacromolecules 10, 1597-602 (2009).
Ghezzi, C. E., Rnjak-Kovacina, J., Weiss, A. S. & Kaplan, D. L. Multifunctional Silk Tropoelastin Biomaterial Systems. Isr. J. Chem. 2006, n/a-n/a (2013).
Fink, H. et al. Bacterial cellulose modified with xyloglucan bearing the adhesion peptide RGD promotes endothelial cell adhesion and metabolism-a promising modification for vascular grafts. J. Tissue Eng. Regen. Med. 5, 454-463 (2011).
Zeng et al. "Reviewing the trends of nursing doctoral thesis research in Hong Kong". Open Journal of Nursing. Dec. 2012, pp. 346-350.
Zeng et al. "Bacterial cellulose films: influence of bacterial strain and drying route on film properties." Cellulose, vol. 21, No. 6, Dec. 24, 2014 (Dec. 24, 2014) pp. 4455-4469.
Budtova et al. "Cellulose in NaOH-water based solvents: a review", Cellulose, vol. 23, No. 1, Nov. 5, 2015 (Nov. 5, 2015), pp. 5-55.

* cited by examiner

METHODS OF PRODUCING BIOSYNTHETIC BACTERIAL CELLULOSE MEMBRANES

FIELD OF THE INVENTION

The present disclosure pertains generally to the fields of medicine, microbiology, cell biology and transplantation. More particularly, it relates to methods of producing biocellulosic membranes with improved properties, and their use in various medical applications.

BACKGROUND OF THE INVENTION

Living membrane materials are an important component of all living cells. There are many important uses for membranes in a wide variety of medical applications, such as heart valve prostheses, small diameter vascular grafts, cardiac patch, dura patch, etc. Common types of membrane materials used in medicine and some challenges they pose are:
- autologous tissue—from the human patient, has limited availability, is uncomfortable for the patient during tissue harvest, and increases infection risks;
- xenograft—from animals, requires animals to produce, have limited control over composition, behavior of final product, and morphology
- synthetics—artificially produced, but historically lack either biocompatibility and/or strength Thus, improved forms of membranes suitable for medical uses are needed.

Biosynthetic bacterial cellulose offers many advantages of xenografts, such as biocompatibility and fibrous structure with the advantages of synthetics such as controlled fabrication. The challenge with traditionally-produced bacterial cellulose membranes has been the inability to make them extremely thin, while retaining sufficient strength. Thus, the ability to develop new chemical and physical processes that permit control of the properties of these compositions, as well as the microstructure of the material, will allow one to modify these structures and properties as suited to each unique application.

SUMMARY OF THE INVENTION

Thus, there is provided a method of producing a cellulose membrane, initially including producing a cellulose construct by culturing bacteria, such as acetic acid bacteria, in a culture media under aerobic conditions supporting biocellulose production, wherein the culture media may be selected from, for example, (i) a glucose-containing media; (ii) a mannitol-containing media; or (iii) a sugar-containing media. A cellulose pellicle may be cultured with a permeable membrane that supports the pellicle, and treated with a caustic solution. A series of dehydration-rehydration operations may be performed on the cellulose pellicle, followed by a final dehydration step, to effect compaction of the cellulose membrane. The membrane, either with or without the compaction steps, may be treated with a solution of sodium hydroxide, urea and water, followed by treatment with acetic acid to create a reconstituted or partially reconstituted cellulose membrane. Prior to or subsequent to compaction and/or reconstitution, the cellulose pellicle may be micropatterned with a biological relevant surface pattern. Producing the cellulose construct may include culturing the bacterium for 1-30 days. The method may further comprise forming a patch, a graft, a shunt or a valve from the cellulose membrane.

Culturing the cellulose pellicles with a permeable membrane may further include use of one or more oxygen permeable membranes, such as an oxygen permeable membrane selected from cellophane, a silicone membrane, a Teflon™ membrane, a ceramic membrane, an ePTFE membrane, thin walled porous plastic, a cellulose membrane, a woven textile membrane or a non-woven textile membrane. The oxygen permeable membranes may be positioned a set distance apart from one another such that cellulose is grown between the membranes, such as where the set distance is 0.5-30 mm, producing a corresponding pellicle thickness of 0.5-30 mm, or where the set distance is 0.5-10 mm, producing a corresponding pellicle thickness of 0.5-10 mm., or where the set distance is 1-5 mm, producing a corresponding pellicle thickness of 1-5 mm., or wherein the set distance is 1, 2, 3, 5, 5, 6, 7, 8, 9, 10, 11, 12, 13, 14, 15, 16, 17, 18, 19, 20, 21, 22, 23, 24, 25, 26, 27, 28, 29, or 30 mm, producing a pellicle of 1, 2, 3, 5, 5, 6, 7, 8, 9, 10, 11, 12, 13, 14, 15, 16, 17, 18, 19, 20, 21, 22, 23, 24, 25, 26, 27, 28, 29, or 30 mm thickness, respectively. Natural air may constitute an oxygen source, or concentrated oxygen between 21% and 100%, or between 97-100%. The cellulose may be cultured at the interface of the media and air or concentrated oxygen, with or without a bounding membrane. The oxygen permeable membrane or membranes may be hollow or hollow with contoured internal adjoining components, and the resulting cultured cellulose pellicle is hollow in shape and has internally adjoining surfaces.

The method may further comprise compressing the cellulose pellicle to reduce water content prior to performing the dehydration-rehydration steps. The bacterium may be, for example, *Komagataeibacter-xylinus*, *Komagataeibacter-europaeus*-T or *Komagataeibacter-hansenii*. The dehydration-rehydration operations may include rehydrating the dried pellicle with water. Compaction of the membrane through dehydration-rehydration may include 1-6 dehydration-rehydration cycles.

The dehydration-rehydration cycles may effect a compaction of about 50%, about 60%, about 70%, about 80%, about 90%, about 95% or 98% as compared to the original membrane thickness.

Reconstituting or partially reconstituting the cellulose membrane may include treating a non-dehydrated, non-compacted wet pellicle, a dehydrated non-compacted pellicle, a rehydrated compacted pellicle, or a compacted dried pellicle with a cellulose-dissolving solution, such as an aqueous solution of sodium hydroxide, urea and water for about 5 minutes to about 6 days, followed by treatment with acetic acid for about 5 minutes to about 48 hours. The sodium hydroxide/urea/water treatment may be performed as follows:
  (a) an initial treatment at a temperature of −8 C to −15 C for 5 minutes to 2 hours;
  (b) an extended treatment at a temperature of 5 C to −15 C for 5 minutes 6 days; and
  (c) a final treatment at a temperature of −8 C to −15 C for 5 minutes to 2 hours.

The sodium hydroxide/urea/water treatment may be performed with respective weight ratios of 2-10:5-20:70-93 for sodium hydroxide:urea:water. The membrane reconstitution or partial reconstitution may further include addition of plant cellulose, and/or chemical treatment of the cellulose membrane to alter one or more of its properties.

Also provided is cellulose membrane produced according to a method as set out above. Also provided is a patch, a graft, shunt or a valve produced according to a method as set out above. Also provided is a kit comprising a cellulose membrane produced according to a method as set out above, or a patch, a graft, a shunt or a valve produced according to a method as set out above.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

DETAILED DESCRIPTION OF THE PREFERRED EMBODIMENTS

Figure 1:
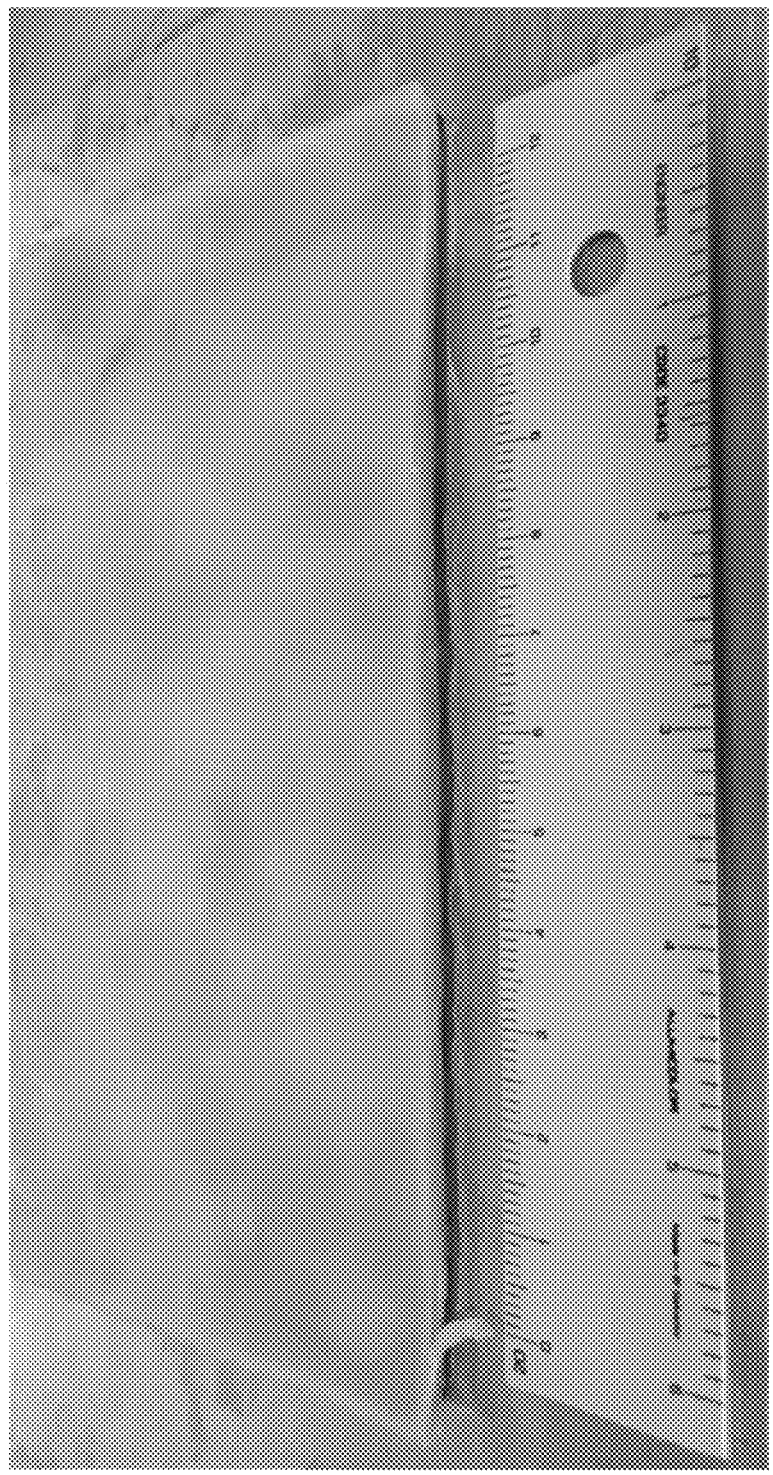
FIG. 1. A cultured planar cellulose pellicle.

The inventors have developed processes that permit production of extremely thin bacterial cellulose membrane without loss of mechanical strength. Further, different applications demand different mechanical characteristics which require the ability to control these properties with reliability. The inventors have further developed a biosynthetic bacterial cellulose membrane material whose morphological and mechanical characteristics may be reliably controlled by tuning chosen parameters of physical and chemical processes during their fabrication. The result is a material with new composition and highly tunable mechanical properties with numerous applications.

These new materials have a variety of potential medical applications: surgical or transcatheter heart valve tissue (aortic, mitral and pulmonary), vascular patch tissue, vascular graft conduit (including small diameter coronary bypass graft), vascular shunts, surgical patch or mesh (hernia, dental, dural, breast reconstruction, pelvic floor reconstruction), temporary dermal tissue covering and general surgical wound care. It is also biocompatible, tunable for particular purposes, and is storage stable.

These and other aspects of the disclosure are discussed below in detail.

I. Definitions

Pellicle, as defined here, means an unprocessed cellulose embodiment or matrix produced between a culture media and an air interface from cellulose producing bacteria in varying thicknesses as is disclosed.

Cellulose pellicle, as defined here, means the equivalent of a pellicle.

Contoured cellulose pellicle, as defined here, means a cellulose pellicle that is produced in a targeted form. This includes forms such as a tube, a curvilinear shape or as a tube with internal or external adjoining features (i.e., heart valve leaflets).

Cellulose membrane, as defined here, means a cellulose pellicle produced from cellulose producing bacteria that has been processed to form a thin membrane. This membrane can be of planar, curvilinear shape, tubular or tubular with internal or external adjoining features.

Reconstituted cellulose membrane, as defined here, means a solid cellulose pellicle membrane that has been dissolved or partially dissolved in solution and coagulated to again form a solid cellulose matrix.

Membrane, as defined here, means an oxygen permeable (i.e. by diffusion) material forming a boundary that cellulose producing bacteria is able to utilize for the production of cellulose upon the boundary.

II. Microbial Biocellulose

It is well documented that certain strains of bacterial microorganisms produce cellulose nanofibers at the interface of media and air in unique layers which together form a pellicle. This phenomenon is ideal to produce intricately interconnected woven constructs beyond the technological capability currently used for processing woven fabrics. These fibers produced from bacteria are inherently pure and highly crystalline. Woven fibrous structures play an integral role in the ability of a matrix to hold sutures and resist tearing. In vitro and in vivo research on microbial biocellulose confirms that due to its biological and physical characteristics it is a "medical quality" material. Thus, microbial (biosynthetic bacterial) cellulose may be able to eliminate problems involving the use of synthetic implants.

Microbial biocellulose consists of $\beta$-1,4 glucan chains, and is chemically identical to plant cellulose. Microbial biocellulose is a highly crystalline cellulose rich in the I$\alpha$ fraction and is synthesized in a reaction catalyzed by the cellulose synthase in the active UDPG form and the allosteric activator c-di-GMP. The cellulose synthase operon is known, as are the functions of the proteins encoded by the genes contained therein. It is a nanoproduct, since it consists of microfibrils some 3 nm across, which form a fibril, known as a strand, which is some 100 nm across. In contrast to phytocellulose, microbial biocellulose is of very high purity, as it is accompanied by no other substances. Basic research regarding glucagon chain polymerization, crystallization and the molecular regulation of synthesis is accompanied by technological studies aimed at optimizing the production conditions of the cellulose material using various culture methods, depending on the final use of the product.

Cellulose strands made by many bacterial cells form an intricately intertwined web, which forms an elastic, highly hydrated pellicle. The pellicle gathers on the surface of the medium in stationary culture. The texture of thusly formed material is reminiscent of the fibrous structure of muscle. The efficiency of the biosynthesis process is dependent on the activity of the producing strain, the composition of the growth medium and the culture conditions.

III. Methods

As discussed in greater detail below, the inventors have developed improved methodologies for preparing and processing biosynthetic bacterial cellulose membranes. In general, four different methodologies can be employed. These fall into the categories described below, namely, cellulose compaction, amalgamation, production of contoured hollow cellulose membranes, and micropatterning. These may be used independently or in conjunction with each other to produce improved forms of biosynthetic bacterial cellulose membranes.

A. Cellulose Pellicle Production

In a first, step, culturing of appropriate bacteria under appropriate conditions produces cellulose in the form of a pellicle. Bacteria that may be employed advantageously include *Komagataeibacter-xylinus*, *Komagataeibacter-europaeus*-T, and *Komagataeibacter-hansenii*-T. Other bacteria include *Acetobacter xylinum*, *Acetobacter pasturianus*, *Acetobacter aceti*, *Acetobacter ransens*, *Sarcina ventriculi*, *Bacterium xyloides*, bacteria belonging to the genus *Pseudomonas*, bacteria belonging to the genus *Agrobacterium*, and bacteria belonging to *Rhizobium*. Preferably a strain of *Acetobacter xylinum* (also designated *Gluconacetobacter xylinus*) is used, such as, but not limited to, *Acetobacter xylinum* NCIB 8246 ATCC (American Type Culture Collection) number 23769, *Acetobacter xylinum* NQ5 ATCC number 53582, or *Acetobacter xylinum* BPR2001 ATCC number 7000178.

Another important factor is the culture conditions. The inventors have determined that several different culture media provide advantageous properties. Example useful culture media include glucose-containing media, mannitol-containing media, and sugar-containing media. It is understood that other culture media, however, may also be useful in culturing cellulose-producing bacteria.

In various media, cultures may be incubated statically at about 20° C. to 35° C. with a starting pH of approximately 3 to 6, and from 1 day to 30 days.

Following culturing, the cellulose pellicles, depicted in FIG. 1, can be physically removed from the culture and treated with a mild caustic solution, such as 1-4% (w/w) sodium hydroxide, to remove any viable bacteria or other microbes. The treated material may then be rinsed with a surfactant such as sodium dodecyl sulfate (SDS), such as 1-10% (w/w) to remove residuals, flushed with distilled water and stored in ethanol or water at 4-20° C. until use.

B. Compaction

An important aspect of the disclosure is the use of a compaction protocol that can produce extremely thin cellulose membranes without any loss of mechanical strength. The initial volume of the pellicle is mostly water, with a small percentage that is actually cellulose. Integral to the technology disclosed for biomedical applications is the ability to make thin constructs while maintaining equivalent mechanical properties.

Figure 3:
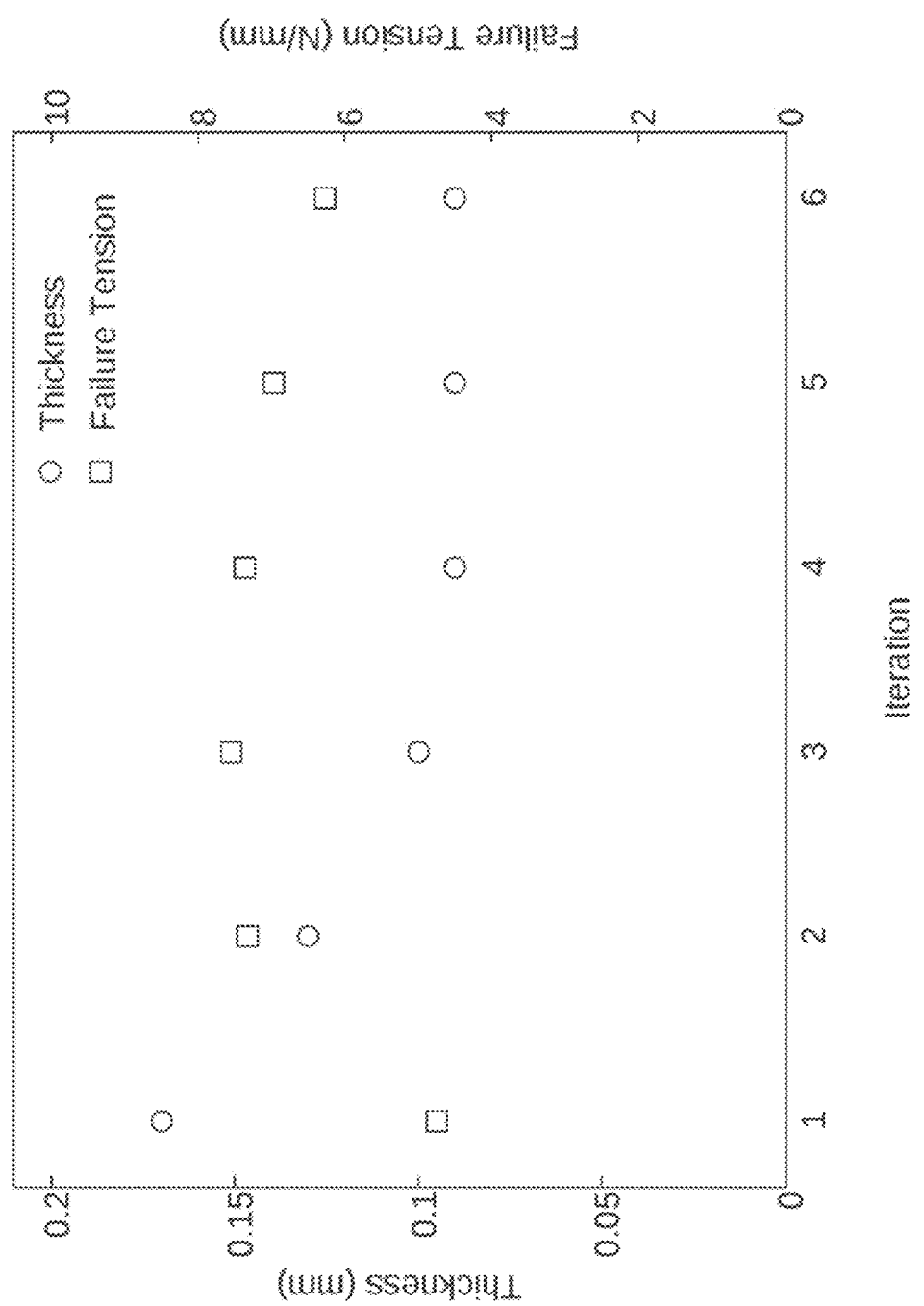
FIG. 3. A chart illustrating the influence of compaction cycles on failure tension.
Figure 4:
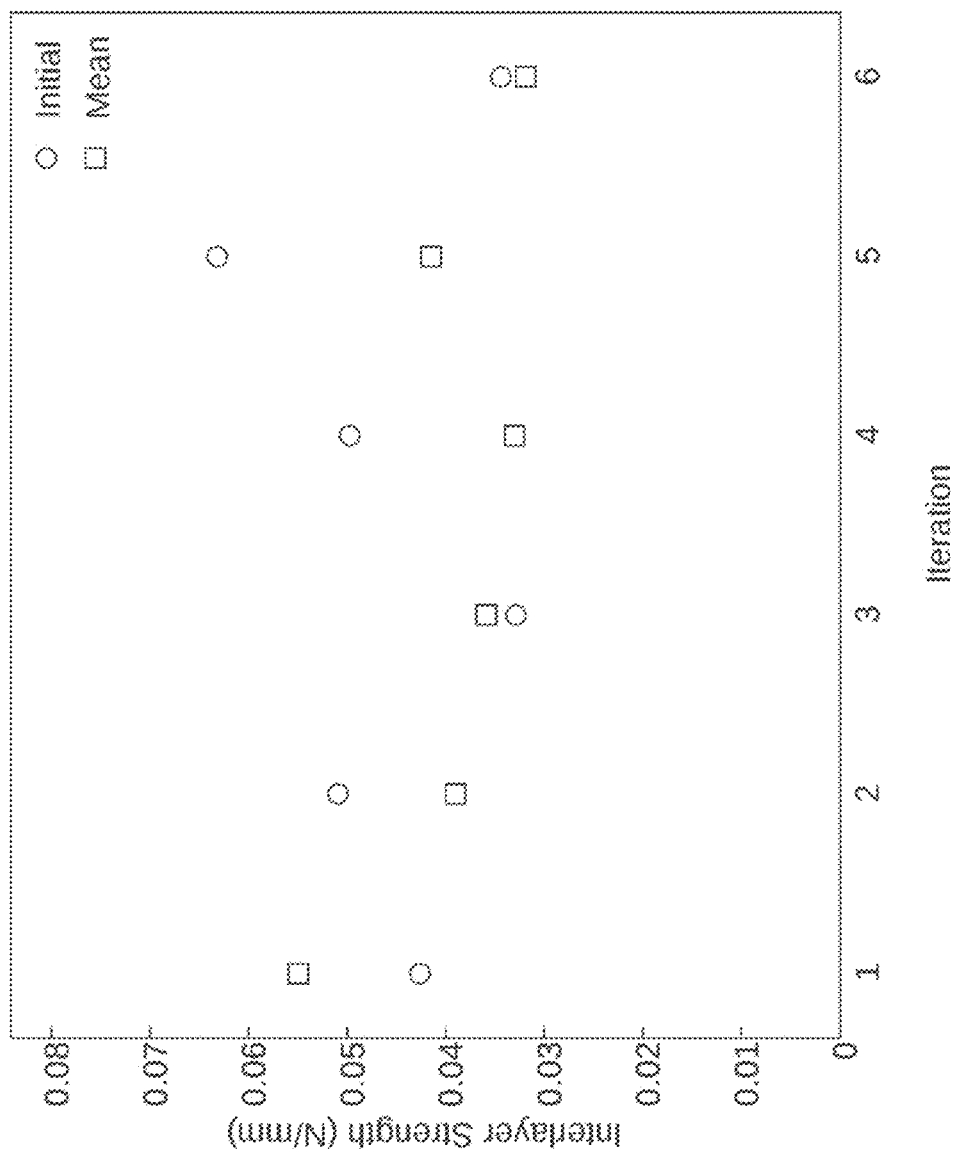
FIG. 4. A chart illustrating the influence of compaction on interlayer delamination strength.
Figure 5:
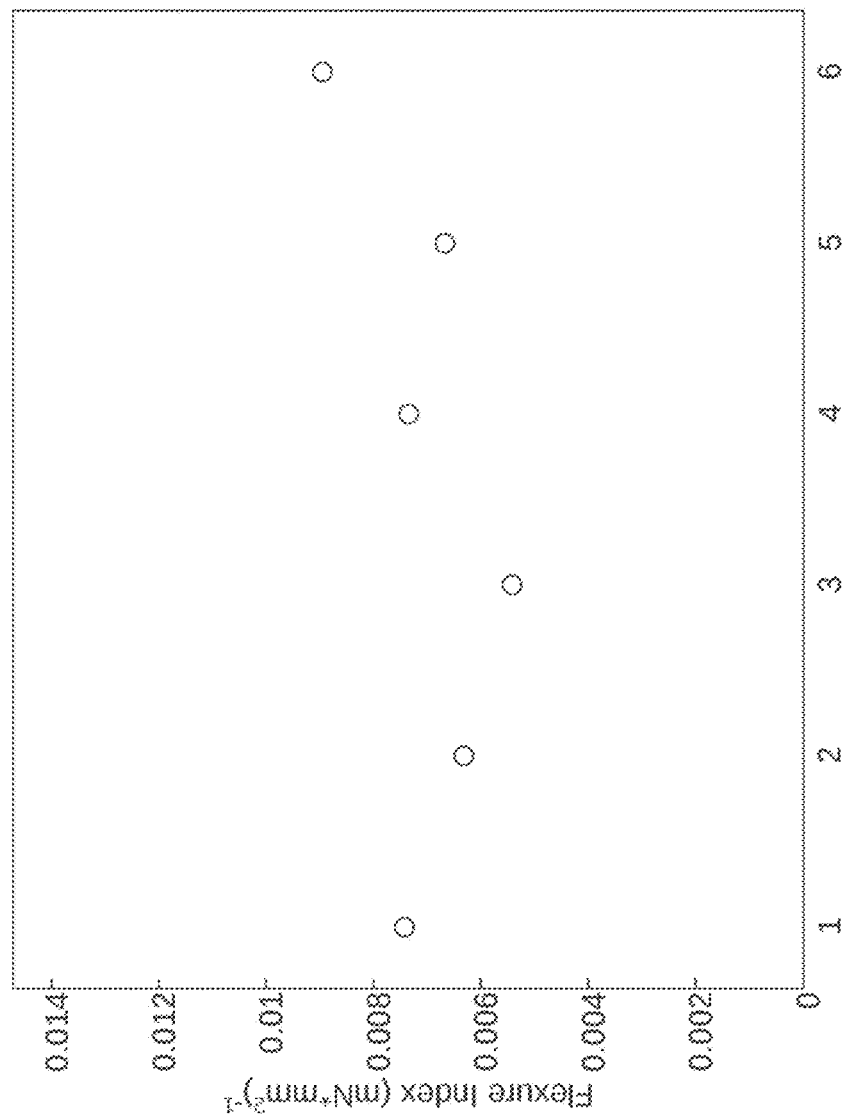
FIG. 5. A chart illustrating the influence of compaction on membrane flexibility.

After production, pellicles are initially dehydrated, for example at about 25-100° C. for approximately 1-24 hours. The dehydrated cellulose membranes are then rehydrated, for example for 1-24 hours, and then dehydrated again at for about 1-12 hours. After initial dehydration, two, three, four, five, six or more iterations of rehydration/dehydration are performed to reduce, or compact, the cellulose membrane thickness. The cellulose membranes can be compacted anywhere from 50% to greater than 98% as compared to initial thickness. The mechanical properties, upon hydration, including inter-layer bonding strength, flexure and failure tension are consistent, if not improved, between compaction iterations as shown in FIGS. 3-5.

C. Amalgamation

A further aspect of the present disclosure is the development of a protocol that creates a ground substance made of reconstituted or partially-reconstituted cellulose that compliments the existing fibrous biosynthetic bacterial cellulose structure to provide significantly improved resistance to delamination. In particular, the inventors have developed a method for improving the inter-layer strength of microbial cellulose membranes. While many cellulose-dissolving substances may be employed in the amalgamation process of the present invention, an aqueous solution of sodium hydroxide, urea and water has been determined to exhibit the ability to dissolve at least cellulose having a molecular weight below (e.g., $1 \times 10^5$) at temperatures ranging from $-10$ to $-15°$ C. This solution with the dissolved cellulose can then be regenerated as a solid construct at room temperature when exposed to a low grade acidic solution. Importantly, the reconstituted material retains its primarily fibrous structure.

For example, a dried cellulose membrane (prepared as discussed above) can be exposed for about 15-60 minutes, to a pre-cooled (e.g., less than $-10°$ C.) solution of sodium hydroxide, urea, and water. The amounts of sodium hydroxide and urea in the solution may be roughly the same, but as a lower amount than the water, such as with a 7:12:81 ratio, respectively, being particularly contemplated. The cellulose membrane is allowed to soak from a few minutes to several days in the solution in cold temperatures (e.g., approximately 0° C.), followed by cooling to approximately $-10°$ C. for 15 to 60 minutes. Some of the cellulose of the membrane dissolves as a result of exposure to the sodium hydroxide/urea water solution, but may remain within the membrane matrix of the non-dissolved cellulose. The cellulose membrane is removed and treated with acid (e.g., 4% acetic acid for 1-48 hours) followed by rinsing. The acid exposure reconstitutes at least some of the dissolved cellulose into a primarily fibrous structure that integrates and/or interacts with the non-dissolved cellulose structure. The dissolution and reconstitution of a portion of the cellulose structure is referred to herein as partial reconstitution. It has been found that this process improves the inter-layer strength of the material. Optionally, plant cellulose may be dissolved with the cellulose-dissolving solution prior to treating the bacterial cellulose. This presence of additional dissolved cellulose may penetrate the bacterial cellulose membrane to further improve the properties or surface characterization. Such chemical treatment allows for control over hydrated mechanical properties including inter-layer bonding (peel) strength, tensile strength and elastic behavior as depicted in FIGS. 6 and 7.

It is contemplated that the amalgamation procedure may be employed on any of non-dehydrated, dehydrated, or rehydrated cellulose pellicles, including either compacted or non-compacted cellulose pellicles.

Figure 6:
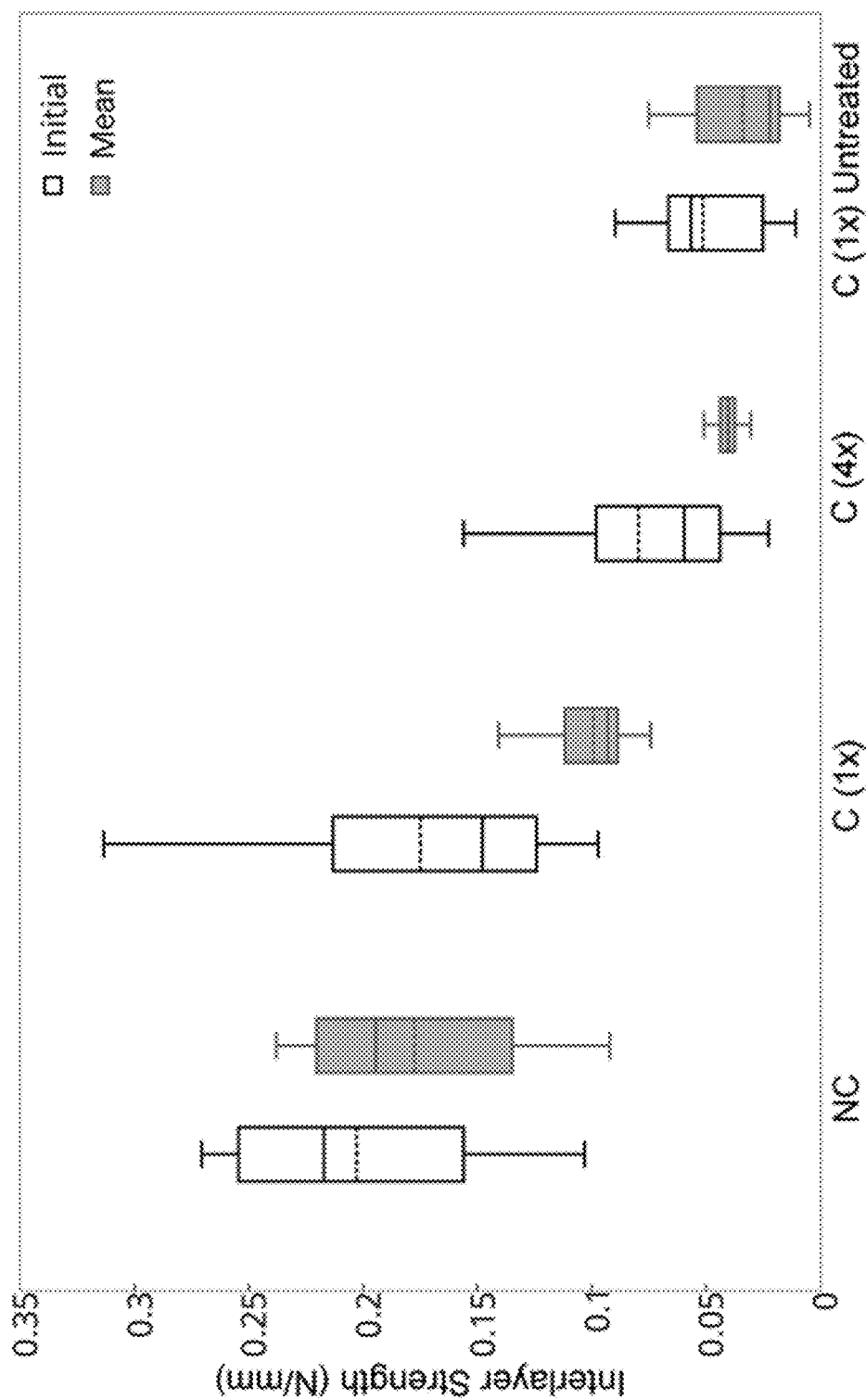
FIG. 6. A chart illustrating the influence of amalgamation treatment on interlayer delamination strength.

FIG. 6 illustrates the impact of amalgamation treatment on various pretreatment materials including: (i) a non-compacted (NC) biosynthetic bacterial cellulose pellicle; (ii) a compacted (C) biosynthetic bacterial cellulose membrane; (iii) a biosynthetic bacterial cellulose membrane after four compaction cycles; and (iv) an untreated (non-amalgamated) compacted biosynthetic bacterial cellulose membrane.

Figure 7:
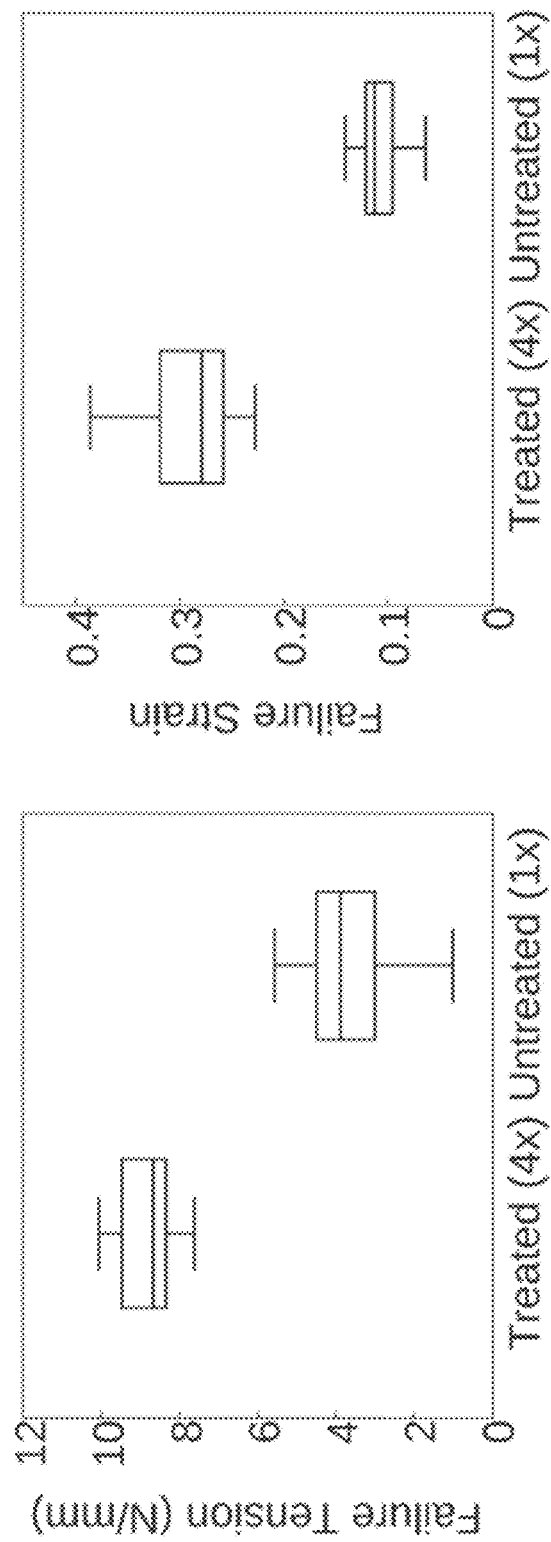
FIG. 7. A chart illustrating the influence of amalgamation treatment on the failure tension and failure strain of cellulose membranes.

FIG. 7 illustrates the influence of amalgamation treatment on failure tension and failure strain.

D. Contoured Hollow Matrix Production

Figure 2:
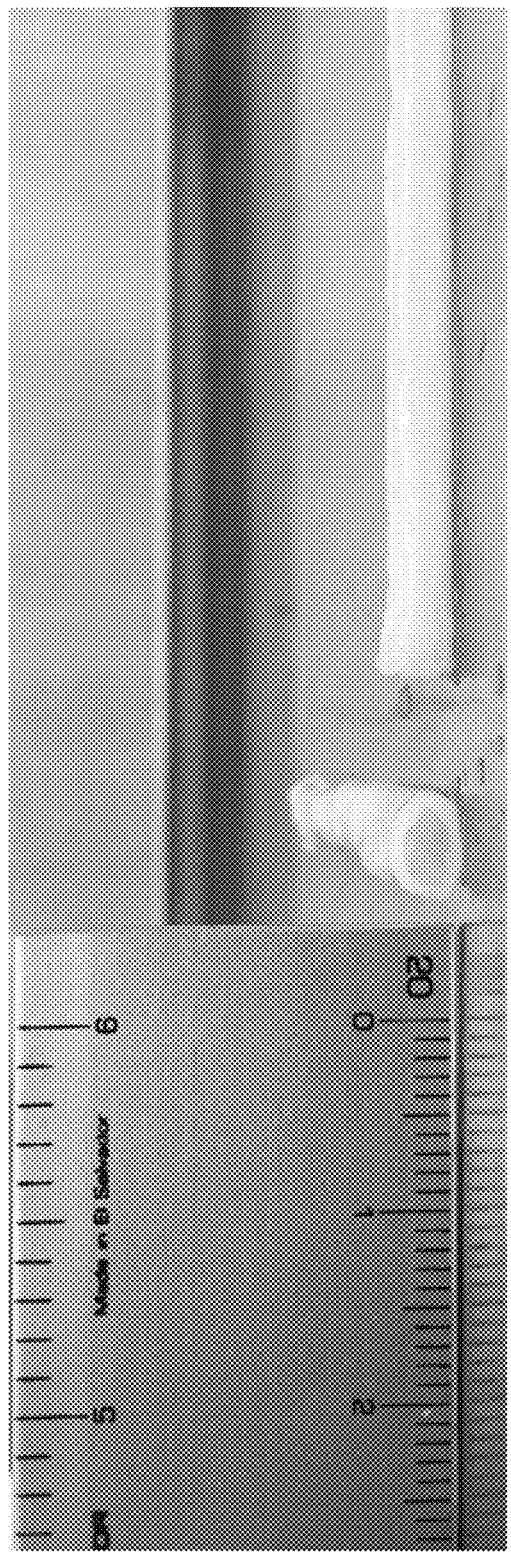
FIG. 2. A cultured hollow cellulose tube.

Another important aspect of the disclosure is the production of biosynthetic bacterial cellulose membranes in the form of a cylindrical construct, as shown in FIG. 2, thus permitting applications where such constructs are needed without the need for physical constructions (e.g., sutures) using flat sheets of cellulose membrane material. This unique improvement has particular value in the creation of cylindrical bypass grafts and stent coverings. For devices such as heart valves, pericardial tissue is laser cut from flat sections and sewn to a stent in the form of valve leaflets. The ability to make these as a single contoured solid construct is a tremendous advantage for heart valve or related applications by minimizing required suturing.

Prior methods utilize multiple techniques. Of most relevance is the use of an oxygen permeable membrane with gas on the inside of the membrane and with inoculated media on the outside. The approach described here is unique in that an oxygen permeable membrane is also used as a culture boundary, thereby providing control over wall thickness (e.g., from about 0.5 mm to 10 mm) and quality (e.g., reduce variations in thickness, control fiber orientation) of the cultured cellulose membrane being fabricated. Such permeable membranes can vary and may include silicones, Teflon, ceramic, ePTFE, porous plastics, cellulose and woven or non-woven textiles. Oxygen gas ranging from 21% (natural air) to 100% $O_2$ can be used as the oxygen source for cellulose production. A mold is used to trap inoculated media between two permeable membranes. This allows oxygen to permeate from both sides of the culture media which encourages bacterial cellulose production in two directions rather than one. Additionally, the distance between membranes can be varied to produce contoured pellicles of variable thicknesses. This method can be used to make tubular cellulose pellicles of internal diameters ranging from about 1-50 mm. It can be used to make a pellicle with a curvilinear shape such that it fits part of a blood vessel or to target specific reconstruction surgery applications. Or a tubular pellicle of diameter ranging from about 15-40 mm with internal or external adjoining features (i.e., heart valve leaflets) can be formed.

Figure 8:
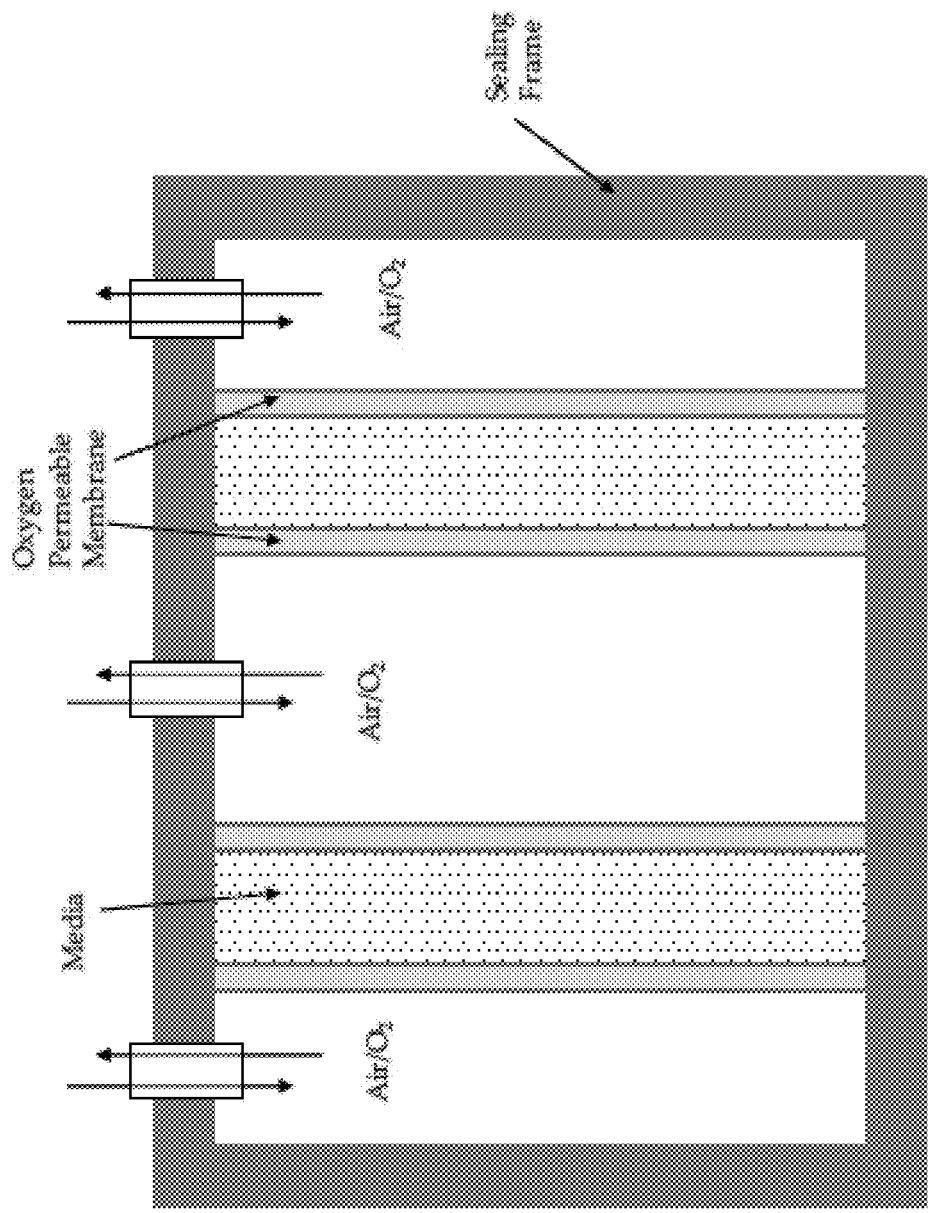
FIG. 8. A schematic illustration of a membrane bioreactor.

A bioreactor with cylindrical oxygen permeable membranes provides a specific example of a bioreactor cross-section with two such cylindrical membranes as illustrated in FIG. 8, spaced at an appropriate distance. Because the media thickness is controlled by the bounding membranes, the final wet thickness of the cellulose pellicle is also controlled. Post-culture treatments include mild base (e.g., 1% NaOH) and SDS (e.g., 5%) to destroy pyrogens and viable microorganisms, followed by rinsing. The construct can then be set over a solid mold, potentially using initial pressure to compress excess water from the construct. The pellicle may be dehydrated over the mold in order to define the final dehydrated shape. Repeat hydration-dehydration cycles as discussed above may be performed as desired to reduce thickness. Optional chemical treatment, such as sodium hydroxide, urea and water solution may further improve cellulose membrane properties.

E. Micro-Patterned Contoured Hollow Matrix Production

Yet a further embodiment involves the use of micropatterned molds that allow for controlled orientation of surface-cellulose fibers on cellulose membrane surfaces, rendering them more conducive to endothelial cell attachment and growth. The ability to form a contoured hollow matrix is of particular importance to the creation of vascular conduits and heart valves. Unique to these natural blood conduits is the fact that the cells that line the inner surface and contact blood (endothelial cells) are oriented such that they minimize the fluid shear across the surface. Such orientation behavior has been sought when seeding cells on tissue engineered vascular grafts and dynamically culturing them in a bioreactor. With the ability to form contoured constructs also comes the opportunity to align cellulose formation which will ultimately impact endothelial cell attachment and growth.

Here, the utilization of microfabrication technologies (e.g., micro-patterned substrate which acts as a mold) generates a surface pattern that impacts bacteria growth and movement, which leads to either a patterned cellulose surface layer or uniquely orientated fibers on the cellulose surface. This is primarily useful for tubes or curvilinear shapes. At the submicron level, Electron Beam Lithography for micropatterning of a silicone substrate can be used to generate a mold. Then, silicone is applied across the surface of the mold at a constant thickness. This is then wrapped into a contoured shape and sealed to produce the patterned $O_2$ permeable membrane for culturing. At the micro (1-500 micrometers) level, lasers can be used to produce a patterned surface which can then be used for either culturing or as a mold. This too may be done on a flat surface and then wrapped and sealed. Other options may include laser ablation, laser micro milling/patterning, laser scribing of a permeable membrane surface for direct culturing or on a surface to be used as a mold for casting the permeable surface.

Subsequently, when cells grow on this patterned or fiber oriented surface, they interact with the cellulose and dimensionally align, a desired feature for enhanced biocompatibility. Patterning has the ability to target cellular infiltration and proliferation of endothelial cells, smooth muscles cells or myofibroblasts.

IV. Uses

Biosynthetic membranes are useful in a wide variety of applications. In one aspect, biosynthetic membranes are utilized simply as carriers or barriers, much as they act in nature. For example, membranes are able to selectively transport or exclude biological molecules based on membrane-based transport systems that involve proteins such as transporters and channels. By reconstituting these systems in biosynthetic membranes, one can create highly selective purification systems that have exquisite sensitivity.

Another area of interest is in energy transduction. For example, light-transducing molecules such as chlorophyll or bacteria rhodopsin can be incorporated into synthetic biomembranes that permit transduction of light into energy. Such "biological solar cells" can be used to generate energy in a variety of settings.

A third area in which biological membranes may find use is as platforms for the delivery of various molecules. These include membrane stabilized antibodies, which may be used to remove harmful molecules from fluids either inside or outside of the body. They may also help target other active molecules to the proper location in a subject, which other active molecules are also associated with the membrane, e.g., in a vesicle.

Finally, as discuss further below, membranes may be used as coatings for non-biological medical devices intended for internal use, or the construct of such medical devices or prosthetics de novo. Some of these applications are discuss further, below.

A. Heart Valves

Deficiencies in the material used in valve devices are related to availability, lack of control in production and processing (chemical treatment), and delivery profile (thickness). Bioprosthetic valves—made using xenograft leaflets—that are implanted surgically suffer from leaflet failure over time requiring eventual re-treatment. Current transcatheter valve device innovations are centered around materials that are thinner, reducing delivery size and allowing for additional material on the outside of the stent to improve apposition and reduce paravalvular flow. Additionally, many groups are researching synthetic polymers to improve availability, target morphometric opportunities and allow for chemical modifications to enhance host interactions. These polymers have not yet come to fruition due to inadequate durability and poor biological interaction. Cellulose, on the other hand, has a strong history with biological interaction including sutures, dialysis membranes and burn coverings. The application of the materials described herein can meet a variety of these requirements, as well as being adequate and adaptable material properties for each valve type, with a history of biological use and biocompatibility, and the ability to form the valve as a whole construct targeting variable morphologies.

B. Cardiac Patches, Vascular Grafts and Shunts

Xenograft materials for vascular patches have similar challenges to that of valve material as they are also primarily based on bovine pericardial tissue. Synthetic materials such as polyesters or polyethylenes for patches and vascular grafts and shunts tend to thrombose across the surface and are inelastic, adding strain on sutured or anastomosis sites. Current treatment for small diameter vascular grafts is dependent on the use of the patient's saphenous vein. Vein grafts have a significant risk of intimal hyperplasia affecting patency thus requiring repeat procedures. The materials described herein can be used as a cardiac patch or for small diameter grafts and shunts. With processing and treatment opportunities, the material can be improved by making it more robust while still retaining its natural biocompatible properties.

C. Dural Patch

Dura mater is a membrane situated between the inner side of the skull and the brain. It protects the brain and functions as a conduit for cerebral fluid. The need for patch material arises from damage to this tissue from surgery or disease states. Autologous tissue is harvested from part of the patient's pericranium or fascia lata which adds additional surgical time and patient discomfort. As well, the pericranium tissue may be too small for full defect coverage. Current biological materials utilize material harvested from animals to produce constructs. Cellulose membranes are ideal for this application and are currently being used. Caution has been issued on tensioning sutures in currently marketed bacterial cellulose dura patches. The materials described herein will make for more robust dural patch.

V. Certain Pharmaceutical Materials

In certain embodiments, provided herein are pharmaceutical compositions comprising membranes. In certain embodiments, such pharmaceutical composition comprises a suitable pharmaceutically acceptable diluent or carrier. In certain embodiments, a pharmaceutical composition comprises a sterile saline solution and one or more compounds. In certain embodiments, such pharmaceutical composition consists of a sterile saline solution and one or more compounds. In certain embodiments, the sterile saline is pharmaceutical grade saline. In certain embodiments, a pharmaceutical composition comprises one or more compounds and sterile water. In certain embodiments, a pharmaceutical composition consists of one or more compounds and sterile water. In certain embodiments, the sterile water is pharmaceutical grade water. In certain embodiments, a pharmaceutical composition comprises one or more compounds and phosphate-buffered saline (PBS). In certain embodiments, a pharmaceutical composition consists of one or more compounds and sterile phosphate-buffered saline (PBS). In certain embodiments, the sterile saline is pharmaceutical grade PBS.

In certain embodiments, compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, provided herein are compositions and methods are used in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

VI. Examples

The following examples are included to further illustrate various aspects of the disclosure. It should be appreciated by those of skill in the art that the techniques disclosed in the examples which follow represent techniques and/or compositions discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Matrix Compaction

Microbial cellulose was synthesized by *Komagataeibacter-xylinus* (wild-type) after inoculation of a culture media in an approximate 1:7 ratio from propagation cultures. The Hestrien-Schramm variant culture media was prepared as follows:

| Culture Media | |
|---|---|
| Glucose | 1-10% |
| Peptone | 0.1-3% |
| Yeast extract | 0.1-3% |

| Culture Media | |
|---|---|
| Sodium phosphate dibasic | 0.1-3% |
| Citric acid | 0.1-3% |

Cultures were statically incubated at 30° C. with a starting pH of approximately 3.5 until the time increment was attained. Cultured cellulose pellicles, as seen in FIG. 1, were then removed and treated with a mild caustic solution of 1% (w/w) sodium hydroxide at 75° C. for 2 hours. The treated constructs were then flushed with distilled water to remove residual sodium hydroxide and non-cellulose particulates.

After washing with distilled water, pellicles were placed in a dehydrator at 35° C. for approximately 20 hours. The dehydrated cellulose membranes were then rehydrated by partial or complete submersion in water for at least 24 hours and then dehydrated again at 35° C. for at least 6 hours. This was repeated for 6 iterations. By the third rehydration cycle, the matrix compacted greater than 98% from its initial thickness. Analysis of the mechanical properties indicates that the compaction has no adverse effect on inter-layer bonding strength, flexure or failure tension (maximum force to failure per unit width of cellulose membrane). Failure tension properties indicate that the material after compaction may actually be more unified.

Example 2—Matrix Amalgamation

The inventors have previously developed and optimized culturing and processing methods for producing uniquely thin material and applied these capabilities toward heart valve leaflets, including as set forth in U.S. patent application Ser. No. 14/377,086, assigned to the present assignee, and herein incorporated by reference. During testing, the valve can fail prematurely when sutured in a stent and cycled at FDA standardized pressure gradients. The inventors' investigations indicated this was due to lack of adhesion strength between layers of cellulose. Thus, they have developed a method for improving the inter-layer strength of microbial cellulose membranes. An aqueous solution of sodium hydroxide, urea and water in approximately 7:12:81 ratios has the ability to dissolve cellulose having a molecular weight below ($1\times10^5$) at temperatures around $-10°$ C. This solution can then be regenerated as a solid construct at room temperature when exposed to a low grade acidic solution.

Bacterial cellulose is considered as having fibers with higher molecular weights and as such previous work has utilized plant celluloses such as cotton to attain dissolved cellulose solutions which are later formed into solid constructs. To the inventors' knowledge no one has investigated this treatment and its influence on mechanical properties of microbial cellulose. The inventors investigated the ability of this solution to partially dissolve and later reconstitute some of the fibers inside a microbial cellulose matrix while retaining its primary fibrous structure. Here, a cellulose pellicle was produced from bacteria as described in Example 1, treated with 1% sodium hydroxide, and dehydrated to produce a thin cellulose membrane. The dry cellulose membrane was then exposed, for approximately 30 minutes, to a pre-cooled (less than $-10°$ C.) solution of sodium hydroxide, urea, and water at 7:12:81 wt:wt:wt ratios. The cellulose membrane was allowed to soak for 6 days in the solution at approximately 0° C. followed by cooling to approximately $-10°$ C. for 30 min. The cellulose membrane was removed and soaked in 4% acetic acid for 48 hours followed by flushing with distilled water. This process was able to improve the inter-layer strength of the material.

Example 3—Pellicle Micropatterning

Figure 9:
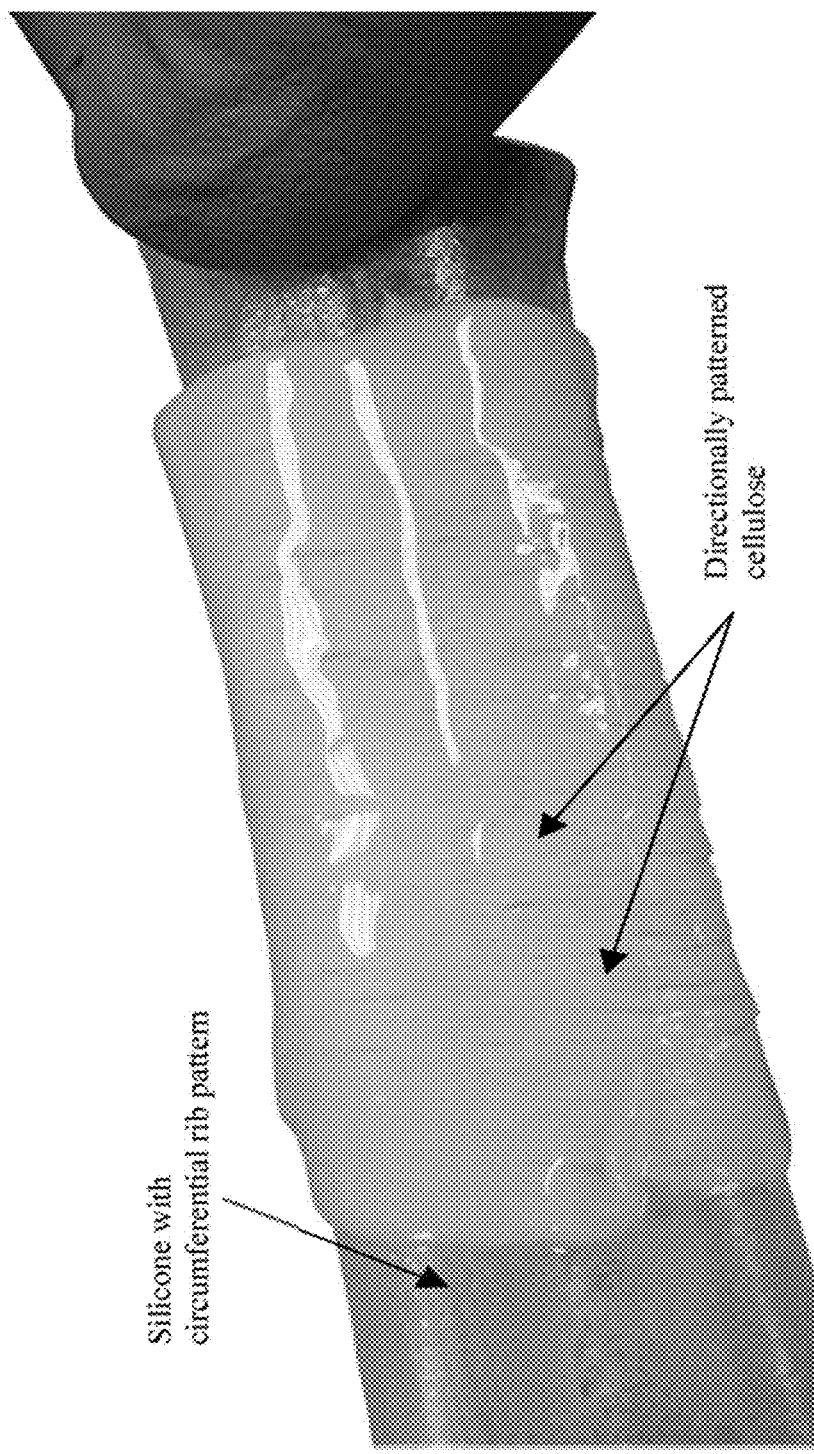
FIG. 9. A directionally patterned cellulose pellicle at a permeable membrane.

A mold with both an inner and outer substantially cylindrical surface was three-dimensionally printed with circumferential ribs. Upon injecting and curing silicone between the printed cylinders, parallel impressions were imparted to the silicone material surface. The molded and impressed silicone tube was then used as an oxygen permeable membrane upon which microbial cellulose was cultured. The cultures were undertaken for 15 days at 30° C. A uniform cellulose pellicle was formed during this time. Inspection of the resulting contoured cellulose pellicle indicated that it had formed with a structure analogous to the underlying pattern, as illustrated in FIG. 9.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods, and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

What is claimed is:

1. A method of producing a biosynthetic bacterial cellulose membrane comprising:
   (a) producing a cellulose pellicle by culturing cellulose-producing bacteria in a culture media under aerobic conditions supporting microbial biocellulose production;
   (b) performing a series of dehydration-rehydration steps on the cellulose pellicle, followed by a final dehydration step, to effect compaction of said cellulose pellicle; and
   (c) subsequent to the final dehydration step, treating the cellulose pellicle with a cellulose-dissolving solution, followed by treatment with acid.

2. The method of claim 1, including providing an oxygen permeable membrane defining a boundary and, prior to step (b), culturing said cellulose pellicle at the boundary formed by the oxygen permeable membrane.

3. The method of claim 2, wherein said oxygen permeable membrane is selected from cellophane, a silicone membrane, a Teflon membrane, a ceramic membrane, an ePTFE membrane, thin walled porous plastic, a cellulose membrane, a woven textile membrane or a non-woven textile membrane.

4. The method of claim 3, including two of said oxygen permeable membranes positioned a set distance apart from one another such that cellulose is grown between the membranes.

5. The method of claim 1, wherein step (b) comprises rehydrating the cellulose pellicle with water.

6. The method of claim 1, including, prior to step (b), treating the cellulose pellicle with a caustic solution to create a wet cellulose pellicle.

7. The method of claim 6, wherein step (c) comprises treating the cellulose pellicle following step (b) with sodium hydroxide, urea and water for about 5 minutes to about 6 days, followed by treatment with acetic acid for about 5 minutes to about 48 hours.

8. The method of claim 1, wherein said cellulose-dissolving solution comprises sodium hydroxide, urea, and water, and wherein step (c) comprises sodium hydroxide/urea/water treatment as follows:
 (a) an initial treatment at a temperature of −8 C to −15 C for 5 minutes to 2 hours;
 (b) an extended treatment at a temperature of 5 C to −15 C for 5 minutes 6 days; and
 (c) a final treatment at a temperature of −8 C to −15 C for 5 minutes to 2 hours.

9. The method of claim 1, wherein step (b) effects a compaction of at least about 50% as compared to the original pellicle thickness.

10. The method of claim 1, wherein step (c) further comprises addition of plant cellulose.

11. The method of claim 1, wherein step (c) further comprises chemical treatment of said cellulose pellicle membrane to alter one or more of its properties.

12. The method of claim 1, further comprising forming a patch, a graft, a shunt or a valve from said biosynthetic bacterial cellulose membrane.

13. A method of producing a biosynthetic bacterial cellulose membrane comprising:
 (a) producing a cellulose pellicle by culturing cellulose-producing bacteria in a culture media under aerobic conditions supporting microbial biocellulose production, wherein a portion of the microbial biocellulose has a molecular weight of less than $1\times10^5$ g/mol; and
 (b) treating the cellulose pellicle with a cellulose-dissolving solution, followed by treatment with acid.

14. The method of claim 13, including, prior to step (b), dehydrating the cellulose pellicle.

15. The method of claim 14, including, prior to dehydrating the cellulose pellicle, treating the cellulose pellicle with a caustic solution.

16. The method of claim 13, wherein said cellulose-dissolving solution includes sodium hydroxide, urea, and water.

17. The method of claim 13, including, prior to step (b), performing a dehydration-rehydration cycle on the cellulose pellicle, including dehydrating the cellulose pellicle, followed by rehydrating the cellulose pellicle.

* * * * *